(12) United States Patent
Connolly

(10) Patent No.: US 6,171,231 B1
(45) Date of Patent: Jan. 9, 2001

(54) URINARY INCONTINENCE DEVICE

(76) Inventor: John G. Connolly, 76 Grenville Street, Toronto (CA), M5S 1B2

( * ) Notice: Under 35 U.S.C. 154(b), the term of this patent shall be extended for 0 days.

(21) Appl. No.: 09/321,378

(22) Filed: May 27, 1999

Related U.S. Application Data

(62) Division of application No. 08/860,265, filed as application No. PCT/CA95/00717 on Dec. 19, 1995.

(30) Foreign Application Priority Data

Dec. 19, 1994 (GB) ................................. 9425578

(51) Int. Cl.[7] ........................................ A61F 2/00
(52) U.S. Cl. ................. 600/29; 600/30; 600/32; 128/885; 128/DIG. 25
(58) Field of Search ............. 600/29–32; 128/DIG. 25, 128/885; 604/9; 623/66.1

(56) References Cited

U.S. PATENT DOCUMENTS

| | | | | |
|---|---|---|---|---|
| 4,154,226 | * | 5/1979 | Henning et al. | 600/32 |
| 4,210,132 | * | 7/1980 | Perlin | 600/32 |
| 4,258,705 | * | 3/1981 | Sorensen et al. | 600/30 |
| 4,679,546 | * | 7/1987 | Van Waalwijk An Doorn et al. | 600/30 |
| 4,904,256 | * | 2/1990 | Yamaguchi | 128/DIG. 25 |

* cited by examiner

Primary Examiner—Cary O'Connor
Assistant Examiner—Michael Astorino
(74) Attorney, Agent, or Firm—Ladas & Parry

(57) ABSTRACT

A urinary incontinence device includes an occluding member, such as a tampon or plug that is retained by magnetic forces acting between a support and magnetic inserts located adjacent the urethra. The insets may be implanted or injected and hold the occluding member in place.

14 Claims, 4 Drawing Sheets

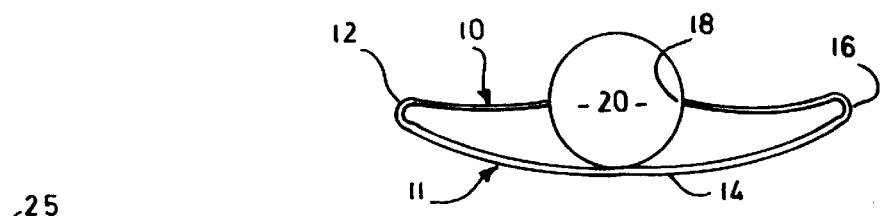
FIG. 1
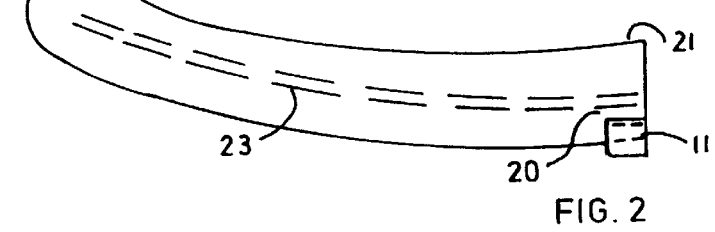
FIG. 2
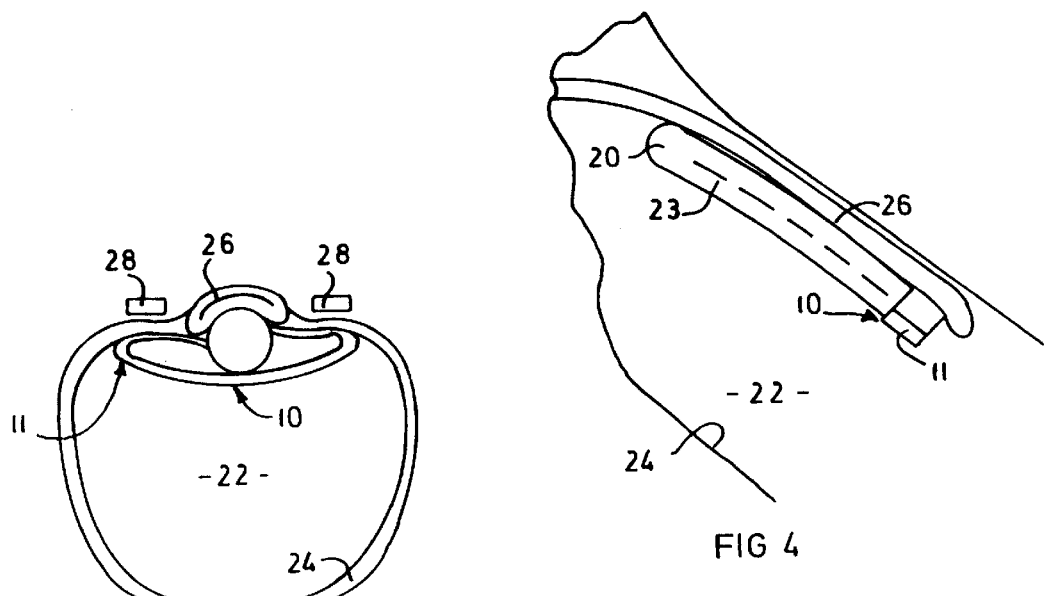
FIG 3
FIG 4

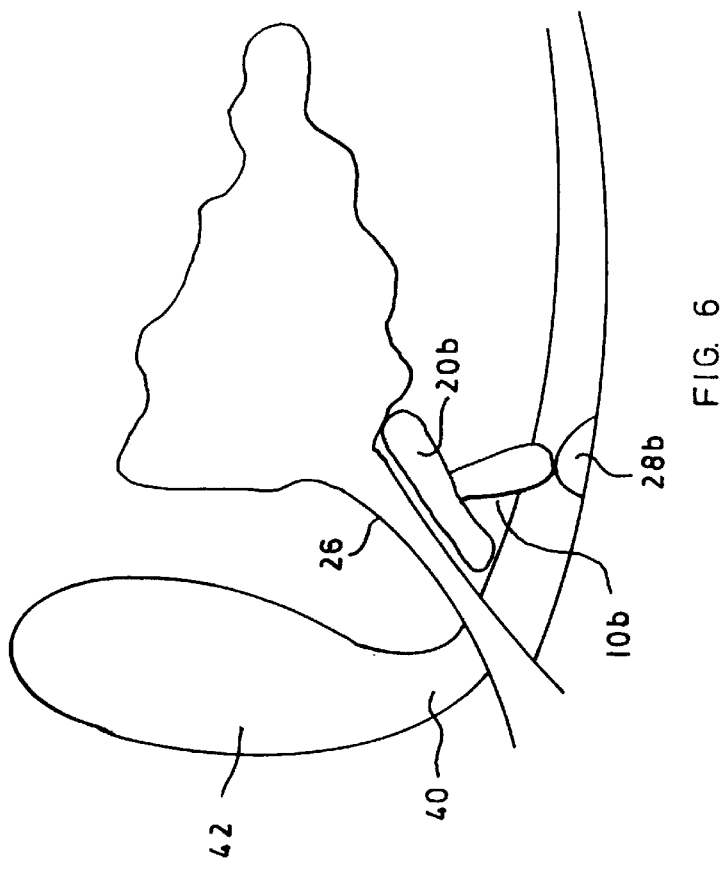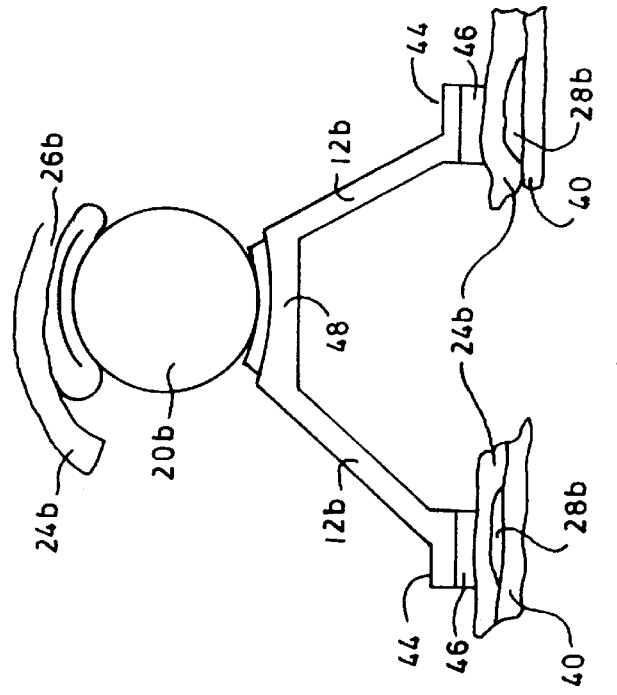

URINARY INCONTINENCE DEVICE

This application is a division of U.S. Ser. No. 08/860,265 filed Aug. 18, 1997 which is a U.S. national completion of International Application PCT/CA95/00717 filed Dec. 19, 1995; which U.S. application is hereby incorporated herein by reference.

BACKGROUND OF THE INVENTION

The present invention relates to a urinary incontinence device.

Urinary incontinence in the aged population is an enormous problem. Approximately 50% of the patients residing in nursing homes were placed there because of problems with urinary incontinence. It is estimated that there are 20 million incontinent patients in the United States alone, and that only 10% of these people ever seek medical assistance. Sufferers from this condition can become social hermits because of the fear of accidents due to sudden loss of urine and the embarrassment associated with urine odours. Most patients have been convinced that incontinence is a natural aging phenomenon and many wear protective padding. This arrangement is extremely primitive and demeaning for the patients.

The majority of urinary incontinence occurs in the female. Recently there has been an increase in post prostatectomy incontinence, since radical prostate surgery has increased dramatically in the last five years.

A distinction must be made as to whether the problem occurs in an active healthy person or in someone who is institutionalized in either a chronic care facility or in a nursing home. The treatment approaches will necessarily be different. In the case of the institutionalized person suffering from urinary incontinence, they are often unable to have any surgical procedure to correct their condition so that non-invasive (non-surgical) approaches are required. The common practice in most nursing homes at present is to have the patients fitted with an absorbent diaper-like material. These antiquated arrangements account for the malodorous environment found in nursing homes as well as the high incidence of local skin problems due to the constant exposure to urine. For various reasons, most nursing homes will not accept patients with catheters.

Many devices have been designed to deal with the problem of urinary leakage and the various difficulties associated with the use of these devices are well known. The basic problem found in many of the females with urinary incontinence is that there is a descent of the bladder neck and an associated wide open bladder neck and upper third of urethra, the so-called funnel-shaped urethra. To correct the incontinence without surgery, one must have a device which either occludes the urethra or elevates the bladder neck and occludes the upper ½ of the urethra. Many of the proposed devices are designed to be placed in the vagina but retaining the device has been one of the main problems associated with their use. In an effort to increase the obstruction to the flow of urine, various other techniques have been used. More recently periurethral injections with various compounds have been used. The purpose of these injections is to obliterate the lumen of the urethra and thus reduce the urinary incontinence. Some of the substances injected include periurethral Teflon, injections of collagen and more recently periurethral injections of autogous fat. In some instances, urethral catheterization has been used to control incontinence. This carries a risk of significant infection. More recently, there have been various urethral plugs designed for inserting in the urethra to occlude the lumen. These plugs are disposable and have to be re-inserted after each voiding. Some of the plugs are retained by means of a balloon arrangements and these all carry the risk of urethral irritation and infection.

In summary, females are incontinent of urine for several reasons and there are various classifications of the problem. As a general observation, the condition can be controlled by several non-surgical approaches. One can insert a urethral plug to retain the urine or a device can be used to elevate the bladder neck and occlude the upper half of the urethra. This will restore continence in most instances.

In German Patent Application No. 3139811, there is described a device in which a magnetic plate is surgically attached to the pubic bone. A tampon containing a magnet is inserted into the vagina and it is intended that the magnetic force between the plate and magnet will occlude the urethra. Test results indicate that this procedure has not been successful in all instances, possibly because of the spacing between the plate and magnet. Moreover, it is clearly desirable for the tampon to be disposable so that the inclusion of the magnet renders the procedure prohibitively expensive.

There have been other proposals to utilize magnetic attraction to retain a medical device, such as that shown in U.S. Pat. No. 4,154,226 or U.S. Pat. No. 3,952,726, both to Hennig, and U.S. Pat. No. 4,258,705 to Sorenson but these have not specifically addressed devices that are intended to overcome the practical problems associated with incontinence.

U.S. Pat. No. 3,926,175 shows a mechanical device intended to supplement bladder control but requires surgical implantation about the neck of the bladder and the application of an external mechanism to open or close the device. As such, its installation and operation is unduly complicated.

A further device is shown in U.S. Pat. No. 2,649,086 which includes a resilient ring with a radial protrusion that is inserted in the vagina and bears against the urethra. However, the careful placement of this device is critical to its successful operation and its retention is dependent purely upon the resilience of the ring.

There are several basic requirements that must be satisfied in the design of these incontinent devices. The device must be held in place and this applies whether the urethra is occluded internally or the bladder neck and upper urethra are occluded by a vaginal device. In either instance of the device, provision must be made for the bladder to be emptied on a regular basis. In some circumstances it is preferable that this should be done without having to remove the appliance. The devices presently available do not meet such requirements satisfactorily and it is therefore an object of the present invention to obviate or mitigate the disadvantages present in such devices.

SUMMARY OF THE INVENTION

In general terms, the present invention provides an incontinence device which may be positioned to occlude the urethra and is retained in position by magnetic forces.

Although magnetic materials have had widespread industrial and domestic applications. They have had limited application in the design of biomedical devices principally because they lost magnetic power when implanted. The discovery of rare earth magnets has opened up a new area for biomedical research. These magnets containing neodymium boron and other compounds are readily available. Their attractiveness lies in the fact that they are up to 50 times stronger than the strongest ferrite or alnico magnets. The rare earth magnets are non-toxic and can be coated with biocompatible materials. This will allow them to be placed in the body and they do not lose their magnetic properties when coated.

The preferred embodiment of devices to be described utilize the power of the neodymium magnets and the numerous biocompatible materials which are available to design effective anti-incontinence devices. To complete the magnetic attachment, metallic depots can be established in various areas in the tissues of the female pelvis by injecting metallic material coated with biocompatible compounds. During the last 10 years, there are many reports of Teflon, collagen or fat being injected around the bladder neck and upper urethra in the female in an attempt to correct urinary incontinence. It is now possible to create metallic depots which will serve as anchoring stations for magnetic attachments of the incontinence devices. It is also possible to establish metallic depots in the vagina without injection by means of a pasted or incorporated into a small tampon.

In one preferred embodiment, a malleable support is provided to retain a tampon within the vagina. The support is retained by deposits of magnetic material injected into the vaginal wall and co-operating with magnets carried by the support. Accordingly, the support can be configured to suit individual needs but is retained securely by the magnets. Preferably the tampon is disposable.

In an alternative embodiment, an incontinence device includes an outer sheath to be secured within the urethra. A core is provided within the sleeve and is retained by magnetic forces between the sleeve and core.

DESCRIPTION OF THE DRAWINGS

Embodiments of the invention will now be described by way of example only with reference to the accompanying drawings, in which FIG. 1 is an elevation of a first embodiment of an incontinence device;

FIG. 2 is a side elevation of the device of FIG. 1;

FIG. 3 is a view showing the device of FIG. 1 installed in a female;

FIG. 4 is a side view of FIG. 3;

FIG. 6 is a side elevation of a further embodiment of an incontinence device;

FIG. 7 is an end view of the device of FIG. 6;

DESCRIPTION OF THE PREFERRED EMBODIMENTS

Figure 5:
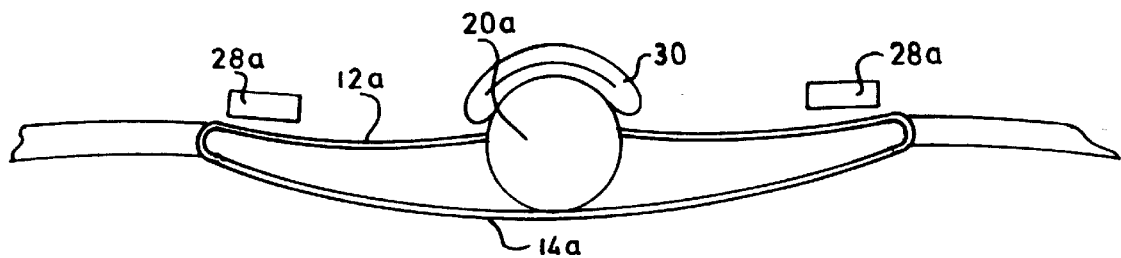
FIG. 5 is a view similar to FIG. 3 showing a second embodiment of the device installed in a male.

Referring therefore to FIG. 1, an incontinence device 10 comprises a band 11 which has opposite ends folded back upon itself to define upper and lower arms 12,14 respectively that are interconnected at opposite ends as indicated at 16. Each of the arms 12,14 is formed from a flexible material that is rendered magnetic, either by a magnetic coating or by selection of the material used to manufacture the arms. Preferably the band 11 is malleable to permit "fitting" of the device 10. The arms 12,14 are covered by a biocompatible material, typically a polymer.

An occluding tampon 20 is located between opposed ends of upper arm 12 and is supported by the central portion of lower arm 14. Notches 18 may be formed in the side of the tampon 20 to locate the ends of arms 12. The tampon 20 has a convex upper surface 21 in section and is formed of Teflon or other synthetic or natural material that is soft enough to conform to the urethra.

The tampon 20 is elongate, as seen in FIG. 2, and has a predefined curvature along its longitudinal axis to conform to the vaginal/urethral wall. Typically the curvature presents a concave upper generatrix. The tampon 20 is resilient so as to provide a gentle lifting force at the distal end when inserted. The resilience is provided either from the material of the tampon itself that is molded or formed with a predefined curvature or from a resilient insert, indicated at 23, that is covered by the material of the tampon. The tampon 20 terminates in a bulbous tip 25 that elevates the bladder neck when in position.

The device 10 is inserted into the vagina 22 to be located adjacent the intersection of the vaginal wall 24 and urethra 26. Magnetic inserts 28 are located in the periurethral tissues on the opposite side of the vaginal wall 24. One of the inserts 28 or arms 12,14 is magnetized and the other is magnetizable so that there is a magnetic attraction between the arms 12,14 and the inserts 28. Assuming the inserts 28 are magnetized, they apply sufficient force on the arms 12,14 to retain the device 10 in the vagina. The tampon 20 is positioned adjacent the urethra 26 so that the convex upper face 21 occludes the urethra. The distal end of the tampon 20 engages the upper wall of the vagina 22 and its resilience and curvature elevates the bladder neck and thereby inhibits fluid flow through the urethra.

To vent the bladder, it is simply necessary to remove device 10 by overcoming the magnetic forces between inserts 28 and arms 12,14 and thereby open the urethra. Alternatively, the tampon may be manipulated to a position in which the urethra is not occluded and the tip 25 allows the bladder neck to fall to void the bladder.

The entire device 10 may be disposable or the band 11 may be reusable with a replacement tampon 20.

The magnetic inserts 28 may be discrete implants of magnetized material or may be localized deposits that are injected or otherwise placed in the periurethral tissues including the adjacent soft tissues, urethral lumen, urethral wall or adjacent bony structures.

Naturally the inserts 28 could be magnetizable material and the arms formed from magnetized material, although it is believed that permanently magnetized implants are preferable. Rare earth magnets, such as neodymium, are preferred for their enhanced magnetic properties. Magnetizable deposits may be provided by iron carbonyl powder dispersed in an injectable carrier.

Tampon 20 is effective not only to occlude the urethra but also to elevate the bladder neck which should be particularly effective to connect urinary incontinence in females.

Notches 18 in the tampon ensure an accurate orientation of the tampon although alternative indicators or orienting arrangements may be utilized.

The device 10 may be modified for use in a male as shown in FIG. 5 in which like reference numerals will identify like components with a suffix 'a' added for clarity.

In FIG. 5, the inserts 28a are located in the scrotal and perineal skin at a location where the urethral lumen is essentially subcutaneous. The arms 12a, 14a are dimensioned to cause the insert 20a to compress the urethral lumen 30. Tampon 20a is similar to that described above although not elongate and is dimensioned to occlude the urethral lumen 30 when applied and retained by inserts 28. Venting of the bladder is accomplished as before by removal of the insert 10.

An alternative embodiment is shown in FIG. 6 with a suffix 'b' added for clarity to denote like components. In the embodiment of FIGS. 1–4, the magnetic inserts 28 are located in the vaginal wall adjacent the urethra. As an alternative, as shown in FIG. 6, the inserts 28b are created on a surface of the inferior ischiopublic ramus 40 of the pelvis 42.

As seen in FIGS. 6 and 7, the device 10b includes a pair of arms 12b, each of which terminates in a foot 44. The foot 44 carries a permanent magnet 46 which co-operates with respective metallic inserts 28b to retain the device 10b within the vagina.

The arms 12b, are malleable and may be made of lightweight metallic materials such as alloys of magnesium or the like or may be made from non-metallic polymer substances and coated with biocompatible material as necessary.

The arms 12b are joined to one another by a bridge 48 that supports a tampon 20b similar to that described above with reference to FIG. 2. The tampon 20 may be secured releasably to the bridge 48 in a manner similar to that shown in FIG. 2 or may utilize a magnetic connection where a suitable magnetic insert is included in the tampon 20.

Device 10b may therefore be inserted in the vagina and retained by the inserts 28b so that the tampon 20 occludes the urethra and elevates the bladder neck.

Device 10b is removable as above for emptying the bladder but preferably tampon 20b will include an opening device that allows the bladder to be emptied without removal of the entire device.

Figure 8:
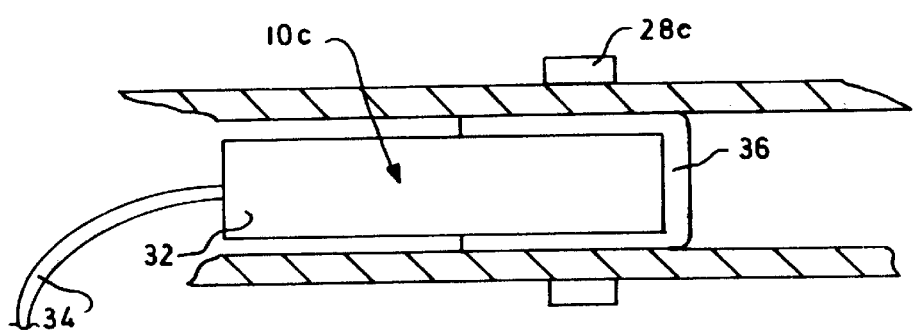
FIG. 8 is a side sectional view of a male urinary incontinence device.

The magnetic retention of an urethral plug is shown in FIG. 8 where like reference numerals are used to denote like components with a suffix 'c' added for clarity.

Device 10c is formed as a plug 32 of foam expandable material that is dimensioned to fit the urethral lumen. A retraction cord 34 is secured to one end of the plug 32 and its opposite end is coated with a circumferential metal band 36. The band 36 may be magnetized or magnetizable.

The plug 32 is retained by magnetic inserts 28c disposed in the urethral wall either by discrete insertion or injection as preferred. Where the band is magnetized, the inserts are magnetizable and, conversely, when the inserts are magnetized, the band is magnetizable.

Figure 9:
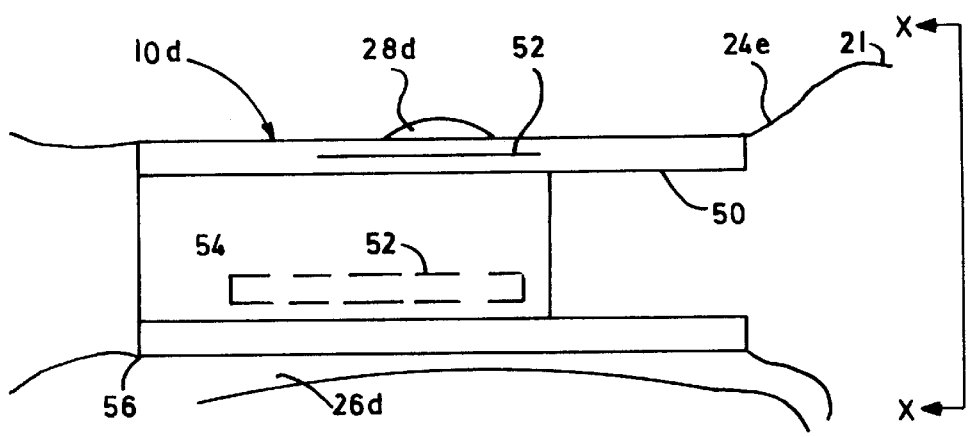
FIG. 9 is a side view of an alternative embodiment of incontinence device for female use.
Figure 10:
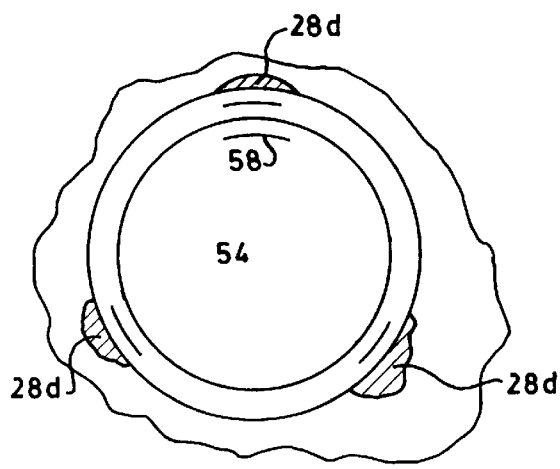
FIG. 10 is a view on the line X—X of FIG. 9.

A urethral plug suitable for female use is shown in FIGS. 9 and 10 where like reference numerals denote like components with a suffix 'd' added for clarity.

The device 10d includes an outer sheath 50 intended to be inserted in the urethra and typically 4.5 cm to 5 cm long. The length and diameter will vary with the age group and condition of the patient. The sheath 50 is formed from elastomeric or polymeric materials that are biocompatible or have a biocompatible coating. The outer surface of sheath 50 may also be treated with biological agents that inhibit production of bacterial biofilm. Magnetic strips 52 are incorporated into the sheath 50 that are at circumferentially spaced locations and are positioned to co-operate with inserts 28d provided in the periurethral wall or vaginal wall.

A core 54 is dimensioned to be insertable in and occlude the sheath 50. A flange 56 is provided at the vaginal end of the core 54 to permit rotation of the core 54 in the sheath. The core 54 is of course effective to seal the sheath and inhibit egress from the bladder.

The core 54 may be retained by a mechanical locking device that is locked or unlocked by rotation of the core or may utilize magnetic forces for retention as shown in FIGS. 9 and 10.

A magnetic strip 58 is incorporated into the outer surface of core 54 and co-operates with the strips 52 in the sheath. Alignment of the strips 52,54 provides a magnetic attraction to retain the core 54 and rotation of the core 54 moves the strips out of alignment to release the core.

In the device 10d, the character of the strips 52,58 and inserts 28d are selected to that effective magnetic interaction is obtained. Typically, the strips 52 will be magnetized and the inserts 28d and strips 58 will be magnetizable. The converse may be selected although care should be taken with the polarity of the magnets.

The provision of the sheath 50 avoids the irritation that might otherwise occur with repeated insertion and removal of the core in the urethra.

Figure 11:
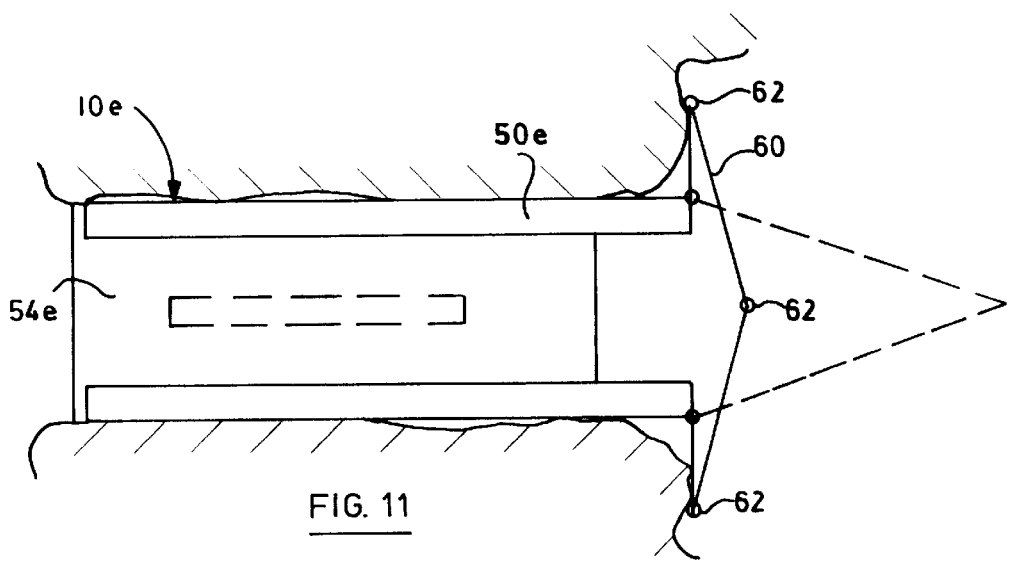
FIG. 11 is a side view similar to FIG. 9 of an alternative device.

An alternative manner of retaining the sheath is shown in FIG. 11 where a suffix 'e' is used to denote like components.

In the device 10e, the sheath 50e is retained by a folding tie bar 60 hinged at one end of the sheath 50e. The tie bar 60 is relatively narrow so as not to occlude significantly the sheath and has living hinge points indicated at 62. Hinge points 62 bias the tie bar to lie flat perpendicular to the urethra so as to engage the bladder neck and inhibit removal of the sheath 50e. The tie bar 60 may be extended in the direction of the sheath during insertion by application of a suitable tool along the axis of the sheath and upon release will return to the flat perpendicular orientation.

The core 54e is retained in the sheath 50e in a manner similar to that noted above allowing repeated removal and insertion.

I claim:

1. A urinary incontinence device for applying a compressive force to the urethra and cause restriction thereof, comprising an occluding member having a body with an outer surface, a support to locate said member in a position in which said outer surface applies a compressive force to said urethra to cause and collapse restriction of the urethra and a retainer to secure said support in said position, said retainer including a magnetic portion on said support and at least one subcutaneous magnetic depot whereby said support member is retained in operative relationship by application of magnetic force.

2. A device according to claim 1 wherein said body is detachably secured to said support.

3. A device according to claim 1 wherein a plurality of said subcutaneous depots is provided at spaced locations.

4. A device according to claim 3 wherein said support has a pair of laterally extending legs and said subcutaneous depots are spaced apart at distal ends of respective ones of said legs.

5. A device according to claim 1 wherein each of said depots is provided by iron carbonyl powder dispersed in an injectable carrier.

6. A device according to claim 5 wherein said each of said depots is deposited subcutaneously by injection.

7. A device according to claim 5 wherein said support is malleable and may be adjusted to maintain said member in said location.

8. A device according to claim 1 or 2 wherein said support includes an intra-urethral sleeve and said member is detachably secured within said sleeve to occlude said urethra.

9. A device according to claim 8 wherein said member is detachably secured in said sleeve by application of magnetic forces therebetween.

10. A device according to claim 9 wherein said sleeve member is rotatable within said sleeve to align a magnet and magnetizable material.

11. A method of occluding a urethra comprising the steps locating a body with an outer surface in a position to apply a compressive force to occlude the urethra, providing a support for said body and retaining said support to hold said body in said position by application of a magnetic force to said support.

12. A method according to claim 11 including the step of providing a magnetic depot subcutaneously to provide said magnetic force to retain said support.

13. A method according to claim 12 wherein said subcutaneous depots are injected.

14. A method according to claim 13 wherein said depots are iron carbonyl dispersed in an injectable carrier.

* * * * *